US012655470B2

(12) United States Patent
Serizawa

(10) Patent No.: US 12,655,470 B2
(45) Date of Patent: Jun. 16, 2026

(54) INHIBITOR OF NON-SPECIFIC BINDING OF NUCLEIC ACID, HYBRIDIZATION REAGENT AND NUCLEIC ACID HYBRIDIZATION METHOD

(71) Applicant: Toray Industries, Inc., Tokyo (JP)

(72) Inventor: Takashi Serizawa, Kamakura (JP)

(73) Assignee: Toray Industries, Inc., Kamakura (JP)

( * ) Notice: Subject to any disclaimer, the term of this patent is extended or adjusted under 35 U.S.C. 154(b) by 896 days.

(21) Appl. No.: 17/288,908

(22) PCT Filed: Oct. 29, 2019

(86) PCT No.: PCT/JP2019/042394
§ 371 (c)(1),
(2) Date: Apr. 26, 2021

(87) PCT Pub. No.: WO2020/090822
PCT Pub. Date: May 7, 2020

(65) Prior Publication Data
US 2021/0395802 A1     Dec. 23, 2021

(30) Foreign Application Priority Data

Oct. 30, 2018     (JP) ................................ 2018-204036

(51) Int. Cl.
*C12Q 1/6832* (2018.01)
*C12N 15/11* (2006.01)
(52) U.S. Cl.
CPC .......... *C12Q 1/6832* (2013.01); *C12N 15/111* (2013.01); *C12N 2310/18* (2013.01)
(58) Field of Classification Search
CPC ................ C12Q 1/6832; C12Q 1/6876; C12Q 2527/125; C12Q 2525/173; C12Q 2525/204; C12Q 2545/107; C12Q 2565/501; C12N 15/111; C12N 2310/18; C12N 15/11; C12N 15/113
See application file for complete search history.

(56) References Cited

U.S. PATENT DOCUMENTS

2001/0053519 A1 * 12/2001 Fodor ...................... G03F 7/265
                                                        536/24.1
2008/0050728 A1     2/2008 Rogan et al.

FOREIGN PATENT DOCUMENTS

| | | | |
|---|---|---|---|
| AU | 20004203808 | * | 9/2004 |
| JP | 2009-518004 A | | 5/2009 |
| JP | 2010-29174 A | | 2/2010 |
| WO | 03/027328 | | 4/2003 |
| WO | 2013/046033 | | 4/2013 |
| WO | 2017/121494 | | 7/2017 |
| WO | 2008/073960 | | 6/2018 |

OTHER PUBLICATIONS

Naxerova (Proceedings National Academy of Sciences (2014) PNAS | Published online Apr. 21, 2014 | E1889-E1898).*
Mlrbase.org/matrue/mimaTOO27616, dowlnloades Oct. 5, 2024).*
Alles ( Nucleic Acids Research, 2019, vol. 47, No. 7 3353-3364 ).*
Modrek (Nucleic Acid Research (2001) vol. 29, pp. 2850-2859).*
Pride (Scientific American (2020) pp. 1-20).*
Burgin (Journal of Mammalogy, 99(1):1-14, 2018).*
Gimenez (Frontiers in Immunology (2017) vol. 8, pp. 1275).*
Matveeva, O. V. et al., "Optimization of signal-to-noise ratio for efficient microarray probe design," *Bioinformatics*, 2016, vol. 32, pp. i552-i558.
Technical Note, "Implementation of DNA Microarray Hybridization Protocols, Translation of Manual Methods to Tecan Hybridization Station," Tecan Japan Co., Ltd., pp. 1-11, http://www.tecan.co.jp/pdf/technote_hs.pdf.
Pan, S. J. et al., "Outliers involving the Poly(A) effect among highly-expressed genes in microarrays," *BMC Genomics*, 2002, vol. 3, Issue 35, pp. 1-12.
Ku, W.-C. et al., "Dextran sulfate provides a quantitative and quick microarray hybridization reaction," *Biochemical and Biophysical Research Communications*, 2004, vol. 315, Issue 1, pp. 30-37.
Smith, Suncerae I. et al., "Electron transfer dissociation of oligonucleotide cations", *International Journal of Mass Spectrometry*, vol. 283 (1-3): pp. 85-93, Feb. 21, 2009.
Majtán, T. et al., "DNA microarrays—techniques and applications in microbial systems," *Folia Microbiologica*, 49 (6): pp. 635-664, Nov. 2004.
Wu, C. et al., "Short oligonucleotide probes containing G-stacks display abnormal binding affinity on Affymetrix microarrays," *Bioinformatics*, vol. 23(19): pp. 2566-2572, Oct. 1, 2007.
Kourilsky, Philippe et al., "Hybridization on filters with competitor DNA in the liquid phase in a standard and a micro-assay," *Biochimie*, vol. 56(9): pp. 1215-1221, Dec. 1974.
Raoof, M. et al., "Improving the selectivity by using different blocking agents in DNA hybridization assays for SiGe biomolecular sensors," *Microelectronic Engineering*, vol. 111: pp. 421-424, May 2, 2013.
Doluca, Osman et al., "Molecular Engineering of Guanine-Rich Sequences: Z-DNA, DNA Triplexes, and G-Quadruplexes," *Chemical Reviews*, vol. 113(5): pp. 3044-3083, Feb. 7, 2013.
Tanaka, Fumiaki et al., "Specificity of Hybridization Between DNA Sequences Based on Free Energy," *Advances in Biometrics: International Conference, ICB 2007*, Seoul, Korea, Aug. 27-29, 2007, vol. 3892, Chap. 29 (558): pp. 371-379, Jun. 6, 2005.

* cited by examiner

Primary Examiner — Anne M. Gussow
(74) *Attorney, Agent, or Firm* — DLA Piper LLP (US)

(57) ABSTRACT
A non-specific-binding inhibitor enables, in detection of a target nucleic acid by hybridization, effective inhibition of cross-hybridization between the target nucleic acid and complementary strands of sequences similar thereto, which non-specific-binding inhibitor has a stable quality among production lots, and a hybridization method for nucleic acid uses the inhibitor. The non-specific-binding inhibitor for nucleic acid includes a nucleic acid which has a base length of 2 to 11 bases and in which the content of a guanine base(s) and/or methylated guanine base(s) in the entire base sequence is not less than 70%.

9 Claims, 3 Drawing Sheets
Specification includes a Sequence Listing.

| S/N ratio | 1.58 | 2.78 | 1.33 | 1.95 | 2.47 |
|---|---|---|---|---|---|

| S/N ratio | 1.88 | 3.11 | 3.92 | 2.65 | 2.52 | 2.19 | 2.30 |
|---|---|---|---|---|---|---|---|

| S/N ratio | 1.40 | 3.23 | 1.75 | 1.79 | 1.88 |

INHIBITOR OF NON-SPECIFIC BINDING OF NUCLEIC ACID, HYBRIDIZATION REAGENT AND NUCLEIC ACID HYBRIDIZATION METHOD

TECHNICAL FIELD

This disclosure relates to an inhibitor that inhibits non-specific binding in nucleic acid hybridization, a hybridization reagent comprising the inhibitor, a hybridization method for nucleic acid, which method uses the inhibitor, and a detection method for a target nucleic acid, the method comprising the hybridization step.

BACKGROUND

Deoxyribonucleic acid (DNA) and ribonucleic acid (RNA) are nucleic acids carrying biological information. DNA contains adenine (dA), thymine (dT), cytosine (dC), and guanine (dG), and RNA contains adenine (A), uracil (U), cytosine (C), and guanine (G), as bases. DNA and RNA, due to their properties, specifically bind to their complementary strands, which have the complementary sequences. The binding affinity and specificity are realized by the combination of two kinds of specific binding modes: A-T (or U) and C-G. The binding affinity and specificity to the complementary strand are dependent on the order of arrangement and the component ratios of the base types contained in the sequence, the binding chain length, the higher-order structure depending on the base sequence and the like. They are also controlled by external factors such as the temperature of the reaction liquid, the ionic strength in the reaction liquid, and the presence or absence of a nucleic acid denaturing agent such as formamide. The binding of nucleic acid with the complementary strand is called hybridization.

In recent years, studies for prediction or diagnosis of disease development have been carried out based on measurement of the expression levels of particular target nucleic acids in various biological samples. The total number of genes present in a human has been reported to be, for example, not less than 26,000. Further, in recent years, microRNAs, which are short-chain nucleic acids, are attracting attention as untranslated RNAs, and it has been reported that not less than 2600 kinds of microRNAs are present in a human. In particular, microRNAs are increasingly regarded as important players responsible for fine-tuning of gene expression regulation in higher organisms including humans since, for example, one kind of microRNA sequence regulates the expression levels of up to more than 100 kinds of genes. Thus, association of microRNAs with diseases has been intensively studied. It is not easy to find genes associated with diseases from such a vast number of candidate genes. Examples of techniques frequently used for such a purpose include exhaustive search for gene expression using nucleic acid arrays (also called DNA microarrays or DNA chips).

A nucleic acid array comprises, on a supporting substrate, nucleic acid probes having complementary base sequences of a large number of target nucleic acids. The target nucleic acids in a sample extracted from a biological sample are preliminarily labeled with a labeling molecule such as a fluorescent substance, and the labeled target nucleic acids are applied to the nucleic acid array. By allowing hybridization between the target nucleic acids and the nucleic acid probes, the expression levels of the target nucleic acids can be detected as fluorescent signals from the nucleic acid complexes formed. Examples of a method of controlling the binding affinity and specificity between the target nucleic acids and their complementary strands in a nucleic acid array include, as described above, changing of the reaction temperature in the hybridization, and changing of the composition of the hybridization solution. In particular, the composition of the hybridization solution is optimized, and such optimization is an essential technique for specific detection of nucleic acids with a nucleic acid array.

However, in common nucleic acid arrays, complementary strand probes are immobilized on a glass substrate, and the glass has a property that allows adsorptive binding of nucleic acids thereto in a manner non-specific to their sequences. Thus, adsorption of the target nucleic acids to the glass substrate causes an increase in the background signal as a result. When the signal values of the target nucleic acids are low, their detection is difficult because of the high background signal.

Further, when target nucleic acids are to be detected using a nucleic acid array or the like, cross-hybridization may occur between the target nucleic acids and nucleic acids whose complementary strands have sequences similar thereto. In such instances, the cross-hybridizing target nucleic acids may exhibit higher signal values relative to the signal values of the target nucleic acids, leading to difficulty in detection of the expression levels of the target nucleic acids.

In particular, since the genome contains repetitive sequences in which particular sequences are highly repeated, detection of a target nucleic acid in genome sequence analysis is difficult when repetitive sequences of the target nucleic acid cross-hybridize with the nucleic acid probe having the complementary strand of the target nucleic acid, due to an elevated baseline of the measured value.

To suppress the non-specific adsorption to a nucleic acid array substrate, and suppress the cross-hybridization with nucleic acids whose complementary strands have sequences similar to the target nucleic acid, a buffer, salt, hydration agent, nucleic acid denaturing agent and/or the like, and/or further, an inhibitor (blocking agent) of non-specific binding of the nucleic acids, is/are added to the hybridization solution. For example, salmon sperm DNA is one of the most commonly used non-specific-binding inhibitor. Other examples of non-specific-binding inhibitors for nucleic acid include human Cot-1 DNA, E. coli tRNA, PCR amplification products (Japanese Translated PCT Patent Application Laid-open No. 2009-518004), poly-dA (Technical Note, "Implementation of DNA Microarray Hybridization Protocols, Translation of Manual Methods to Tecan Hybridization Station" Tecan Japan Co., Ltd., Pan S. J. et al., BMC Genomics, 2002, vol. 3, issue 35, pp. 1-12), random oligonucleotides, and mixtures thereof (JP 2010-29174 A), which are used by addition to hybridization solutions.

As one of the above-described conventionally used non-specific-binding inhibitors for nucleic acid, salmon sperm DNA is prepared by fragmentation of DNA derived from salmon testes, by sonication or physical shearing treatment. The salmon sperm DNA usually has a molecular weight distribution of several hundred base pairs to several thousand base pairs although the molecular weight distribution varies depending on the provider. The salmon sperm DNA is known to have different properties in the molecular weight distribution and the like depending on the production lot. Human Cot-1 DNA is prepared by shearing treatment of DNA derived from human placenta. Since it is similarly derived from a biological sample, its properties such as the molecular weight distribution vary depending on the production lot. *E. coli* tRNA is tRNA extracted from an *E. coli* homogenate. Since it is derived from a biological sample, its properties may vary among production lots.

Thus, in detection of a target nucleic acid using a non-specific-binding inhibitor derived from a biological sample, the measurement result may be differently affected each time when a different production lot is used. Therefore, for example, the non-specific-binding inhibitor needs to be obtained from a plurality of production lots, and comparison and evaluation need to be carried out among the production lots, to identify a particular production lot(s) with which equivalent measurement results can be obtained, and to provide the production lot(s) in a large amount. Thus, much labor has been required.

In contrast, PCR amplification products and random oligonucleotides give relatively small differences in the quality among production lots since PCR amplification products are produced by PCR amplification, and random oligonucleotides are produced by chemical synthesis. However, in a strict sense, PCR amplification products exhibit different rates of contamination with unintended sequences caused by PCR errors among production lots. Random oligonucleotides, in which chain lengths of not more than 10 bases are commonly used, may also exhibit different base components among production lots. Thus, these non-specific-binding inhibitors are still affected by the differences in the lot.

On the other hand, poly-dA is a DNA composed of a single kind of bases (adenine), and can be chemically synthesized. Therefore, it is expected to exhibit fewer differences among production lots. poly-dA is used to block poly-dT on cDNA, which is produced when mRNA is reverse-transcribed. It has been reported that, when a cDNA sample is evaluated using a nucleic acid array, poly-dA inhibits false-positive signals generated between poly-dT on the cDNA and adenine (A)-rich sequences on the complementary strand probes (Pan S. J. et al., BMC Genomics, 2002, vol. 3, issue 35, pp. 1-12). However, nucleic acid arrays also allow cross-hybridization between various similar sequences, and poly-dA, when it is used alone, cannot be expected to have an inhibitory effect on the cross-hybridization between these various similar sequences. Thus, in Pan S. J. et al., BMC Genomics, 2002, vol. 3, issue 35, pp. 1-12, since human Cot-1 DNA is added at the same time, it can be said that the inhibitory effect on the cross-hybridization between various similar sequences is obtained substantially from human Cot-1 DNA.

As described above, conventionally, in detection of a target nucleic acid by hybridization, there has been no non-specific-binding inhibitor which effectively inhibits cross-hybridization between the target nucleic acid and the complementary strands of its similar sequences, and which has a stable quality among production lots. It could therefore be helpful to provide a non-specific-binding inhibitor that satisfies these properties.

The Applicant hereby incorporates by reference the sequence listing contained in the ASCII text file titled SequenceListing.txt, created Apr. 26, 2021 and having 996 bytes of data.

SUMMARY

I discovered that a nucleic acid containing guanine (G) highly effectively inhibits non-specific binding, and that the nucleic acid has a stable quality among its production lots. I thus provide (1) to (12):

(1) A non-specific-binding inhibitor for nucleic acid, the inhibitor comprising a nucleic acid which has a base length of 2 to 11 bases and in which the content of a guanine base(s) and/or methylated guanine base(s) in the entire base sequence is not less than 70%.

(2) The inhibitor according to (1), wherein the nucleic acid has a base length of 5 to 7 bases.

(3) The non-specific-binding inhibitor according to (1) or (2), wherein the guanine bases and/or methylated guanine bases are guanine bases.

(4) The inhibitor according to any one of (1) to (3), wherein the nucleic acid has a sequence of five consecutive guanine bases.

(5) The inhibitor according to any one of (1) to (3), wherein all bases in the nucleic acid are guanine.

(6) The inhibitor according to any one of (1) to (5), wherein the nucleic acid is DNA.

(7) A hybridization reagent for nucleic acid, the reagent comprising the inhibitor according to any one of (1) to (6).

(8) A method of hybridizing nucleic acid comprising hybridizing a target nucleic acid with a nucleic acid capable of specific binding to the target nucleic acid, wherein the inhibitor according to any one of (1) to (6) is made to coexist in the hybridization.

(9) A method of detecting a target nucleic acid comprising:
a hybridization step of hybridizing the target nucleic acid with a nucleic acid capable of specific binding to the target nucleic acid; and
a detection step of detecting a nucleic acid complex formed by the hybridization step;
wherein the inhibitor according to any one of (1) to (6) is made to coexist in the hybridization step.

(10) The detection method according to (9), which uses a nucleic acid array.

(11) Use of a nucleic acid which has a base length of 2 to 11 bases and in which the content of a guanine base(s) and/or methylated guanine base(s) in the entire base sequence is not less than 70%, as a non-specific-binding inhibitor for nucleic acid.

(12) Use of a nucleic acid which has a base length of 2 to 11 bases and in which the content of a guanine base(s) and/or methylated guanine base(s) in the entire base sequence is not less than 70%, for the production of a non-specific-binding inhibitor for nucleic acid.

My non-specific-binding inhibitor for nucleic acid has an inhibitory effect on non-specific binding, which effect is equivalent to or better than those of conventional inhibitors such as salmon sperm DNA. Moreover, since my inhibitor has a stable quality among production lots, it does not require labor for selection and preparation of production lots. In particular, in detection of a target nucleic acid by hybridization, the inhibitor enables stable realization of a cross-hybridization-inhibiting effect.

DETAILED DESCRIPTION

Figure 1:
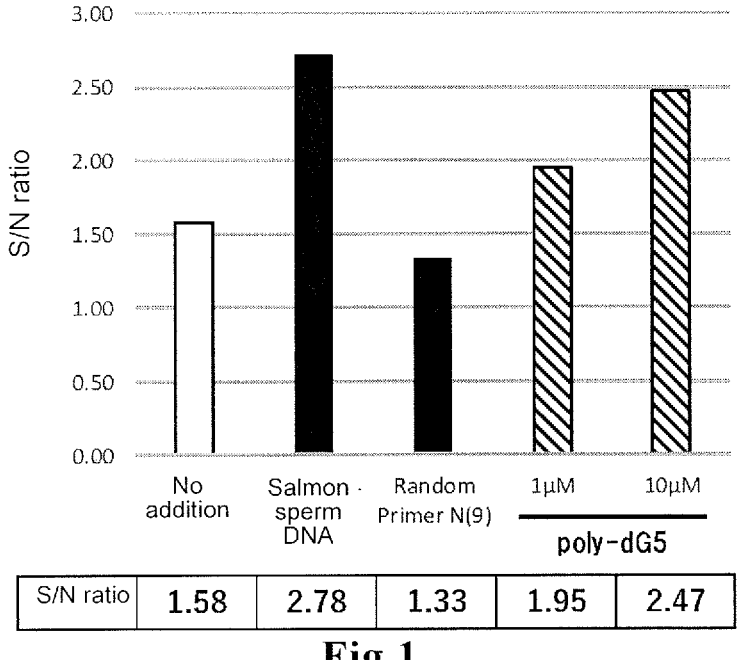
FIG. 1 shows the cross-hybridization-inhibiting effects of salmon sperm DNA, random primers, and poly-dG5 (Examples 1 and 2, Comparative Examples 1 and 2).

I provide an inhibitor that inhibits non-specific binding that occurs in hybridization of a nucleic acid, the inhibitor comprising a nucleic acid which has a base length of 2 to 11 bases and in which the content of a guanine base(s) and/or methylated guanine base(s) in the entire base sequence is not less than 70%. When the nucleic acid contains both a guanine base(s) and a methylated guanine base(s), their total content is not less than 70%. The term "guanine" includes "methylated guanine" unless the context clearly indicates otherwise. However, in the Examples (actual working examples), "guanine" means normal, unmethylated guanine. Normal, unmethylated guanine is preferred to methylated guanine. Examples of the methylated guanine include 7-methylguanine (m7G) and O6-methylguanine (O6-MeG).

The "non-specific binding" of nucleic acid herein means any binding reaction that occurs during hybridization between a target nucleic acid and a nucleic acid (such as a probe) having a sequence complementary to the sequence of the target nucleic acid, except the hybridization involving the target nucleic acid (specific binding).

One example of the non-specific binding of nucleic acid is cross-hybridization that occurs in use of a support (such as a substrate) on which a nucleic acid (nucleic acid probe) used to detect a target nucleic acid is immobilized such as a nucleic acid array (also referred to as DNA microarray or DNA chip), wherein the nucleic acid used for the detection has a base sequence complementary to the target nucleic acid, and wherein the cross-hybridization occurs between the target nucleic acid and a nucleic acid whose complementary strand has a sequence similar to the target nucleic acid. In another example of the non-specific binding, a target nucleic acid adsorbs to the material itself of a support on which a nucleic acid having a sequence complementary to the target nucleic acid is immobilized (wherein the adsorption includes both physical adsorption by the van der Waals force and chemical adsorption by hydrophobic interaction). The "non-specific binding" of nucleic acid includes both of these examples.

The nucleic acid contained in my non-specific-binding inhibitor (also sometimes referred to as "my nucleic acid") has a base length of 2 to 11 bases, more preferably 5 to 7 bases, still more preferably 5 bases. The content of guanine bases in the entire base sequence of the nucleic acid is not less than 70%.

In a preferred example of my nucleic acid, a plurality of guanine bases are consecutively arranged. More preferably, five guanine bases are consecutively arranged.

My nucleic acid may contain a base other than a guanine base, in accordance with the above-described conditions. However, since, when a nucleic acid having a sequence of interest is synthesized by mixing a plurality of bases, contamination with a sequence other than the sequence of interest may occur at a certain probability. Thus, the nucleic acid is more preferably composed of guanine bases alone.

The nucleic acid contained in my non-specific-binding inhibitor may be synthesized by a commonly used nucleic acid synthesis method. Either a solid-phase synthesis method or a liquid-phase synthesis method may be used for the synthesis of the nucleic acid. For example, in a solid-phase synthesis method, modified nucleotide monomers called amidite are immobilized on beads. The synthesis proceeds by addition of nucleotide monomers from the 3'-end side toward the 5'-end side of an oligonucleotide sequence. After completion of extension along the entire chain length, the nucleic acid of interest can be obtained by separation from the solid-phase beads. In a liquid-phase synthesis method, nucleotide monomers are similarly added to a highly dispersible liquid-phase support or the like, to obtain a nucleic acid of interest.

The synthesized nucleic acid may be used after purification by a purification method such as desalting purification, reverse-phase column purification, HPLC purification, or PAGE purification. The nucleic acid used is preferably nucleic acid purified by reverse-phase column purification, HPLC purification, or PAGE purification, more preferably HPLC purification or PAGE purification.

The nucleic acid contained in the non-specific-binding inhibitor may be DNA, RNA, or an artificial nucleic acid. Examples of the artificial nucleic acid include LNA (Locked Nucleic Acid), PNA (Peptide Nucleic Acid), and ENA (Ethylene-Bridged Nucleic Acid). Further, nucleic acids synthesized with a combination of a plurality of nucleic acid types may also be used. Although artificial nucleic acids such as LNA, PNA, and ENA have high enzymatic stability, their production costs are high. Therefore, my nucleic acid is preferably DNA or RNA, more preferably DNA, which has relatively high enzymatic stability. Further, the nucleic acid contained in the non-specific-binding inhibitor may contain inosine (I), in addition to adenine (A), thymine (T), cytosine (C), guanine (G), and uracil (U) as bases.

My nucleic acid may contain a modified base. For example, C may also be contained as 5-methylcytosine (5mC), 5-hydroxymethylcytosine (5hmC), 5-formylcytosine (5fC), 5-carboxylcytosine (5caC) or the like. Further, G may also be contained as 7-methylguanine (m7G), O6-methylguanine (O6-MeG) or the like as described above, or as 2'-O-methylribonucleoside.

My nucleic acid may be modified at one or both of its 5'-end and 3'-end with a phosphate group, an alkyl group, an alkoxy group, an amino group, an adenyl group, biotin, thiol, halogen, fluorescent dye and/or the like. The modifying group(s) is/are not limited to these, and an arbitrary modifying group(s) may be used depending on the intended use.

When the nucleic acid contained in the non-specific-binding inhibitor has a base length of 2 bases or 3 bases, the nucleic acid is composed of guanine bases alone.

When my nucleic acid has a base length of four bases, the nucleic acid is composed of three guanine bases and one arbitrary base (which may also be a guanine base), and the one base is arranged at an arbitrary position in the sequence. When the one base is a guanine base, the sequence is composed of guanine bases alone (that is, the base sequence is "GGGG"), which is more preferred.

When my nucleic acid has a base length of five bases, the nucleic acid is composed of four guanine bases and one arbitrary base (which may also be a guanine base), and the one base is arranged at an arbitrary position in the sequence. Examples of such a nucleic acid include a nucleic acid in which the one base is an adenine base arranged at the third position from the 5'-end (nucleic acid name (DNA): "GGAGG"), a nucleic acid in which the one base is an adenine base arranged at the fourth position from the 5'-end (nucleic acid name (DNA): "GGGAG"), and a nucleic acid in which the one base is a thymine base arranged at the first position from the 5'-end (nucleic acid name (DNA): "TGGGG"). When the one base is a guanine base, the nucleic acid is composed of five consecutive bases all of which are guanine bases (that is, the base sequence is "GGGGG"), which is especially preferred (nucleic acid name (DNA): "poly-dG5").

When my nucleic acid has a base length of six bases, the nucleic acid is composed of five guanine bases and one arbitrary base (which may also be a guanine base), and the one base is arranged at an arbitrary position in the sequence. In particular, the nucleic acid preferably has a constitution containing a sequence of five consecutive guanine bases, and containing the one arbitrary base at either one end. When the one arbitrary base is a guanine base, the sequence is composed of six consecutive bases all of which are guanine bases (that is, the base sequence is "GGGGGG"), which is more preferred.

When my nucleic acid has a base length of seven bases, the nucleic acid is composed of five guanine bases and two arbitrary bases (which may also be guanine bases), and the two bases are arranged at arbitrary positions in the sequence. Preferably, the nucleic acid contains a sequence of five consecutive guanine bases, and contains one arbitrary base at each of both ends, or contains the two arbitrary bases at either one end. When both of the two bases are guanine bases, the sequence is composed of seven consecutive bases all of which are guanine bases (that is, the base sequence is "GGGGGGG"), which is more preferred.

When my nucleic acid has a base length of eight bases, the nucleic acid is composed of six guanine bases and two arbitrary bases (which may also be guanine bases), and the two bases are arranged at arbitrary positions in the sequence. Preferably, the nucleic acid contains a sequence of six consecutive guanine bases, and contains one arbitrary base at each of both ends, or contains the two arbitrary bases at either one end. When both of the two bases are guanine bases, the sequence is composed of eight consecutive bases all of which are guanine bases (that is, the base sequence is "GGGGGGGG"), which is more preferred (nucleic acid name (DNA): "poly-dG8").

When my nucleic acid has a base length of nine bases, the nucleic acid is composed of seven guanine bases and two arbitrary bases (including guanine bases), and the two bases are arranged at arbitrary positions in the sequence. Preferably, the nucleic acid contains a sequence of seven consecutive guanine bases, and contains one arbitrary base at each of both ends, or contains the two arbitrary bases at either one end. When both of the two bases are guanine bases, the sequence is composed of nine consecutive bases all of which are guanine bases (that is, the base sequence is "GGGGGGGGG"), which is more preferred.

When my nucleic acid has a base length of 10 bases, the nucleic acid is composed of seven guanine bases and three arbitrary bases (including guanine bases), and the three bases are arranged at arbitrary positions in the sequence. Preferably, the nucleic acid contains a sequence of seven consecutive guanine bases, and contains one or two arbitrary bases at each of both ends, or contains the three arbitrary bases at either one end. When all three bases are guanine bases, the sequence is composed of 10 consecutive bases all of which are guanine bases, which is more preferred (nucleic acid name (DNA): "poly-dG10"; SEQ ID NO:1).

When my nucleic acid has a base length of 11 bases, the nucleic acid is composed of eight guanine bases and three arbitrary bases (including guanine bases), and the three bases are arranged at arbitrary positions in the sequence. Preferably, the nucleic acid contains a sequence of eight consecutive guanine bases, and contains one or two arbitrary bases at each of both ends, or contains the three arbitrary bases at either one end. When all three bases are guanine bases, the sequence is composed of 11 consecutive bases all of which are guanine bases, which is more preferred (SEQ ID NO:2).

I also provide a hybridization reagent to be used for nucleic acid hybridization, which reagent comprises my nucleic acid.

My hybridization reagent may be prepared as a solution containing my nucleic acid. The concentration of my nucleic acid contained in the hybridization reagent is preferably 0.3 μM to 100 μM. Since a nucleic acid solution with a high concentration has viscosity, the solution is more preferably used at 0.3 μM to 30 μM from the viewpoint of the experimental operation and manufacturing management. The concentration of the nucleic acid may be appropriately selected depending on the intended use and the method of use.

My hybridization reagent may contain a polysaccharide, preferably dextran sulfate sodium. Dextran sulfate sodium can be expected to have an effect which increases the reaction rate of the hybridization since, due to its hydration action, dextran sulfate sodium is capable of mimicking a state where the concentration of the target nucleic acid is increased. The concentration of dextran sulfate sodium is preferably 1 to 30% by weight, more preferably 1 to 20% by weight. It is most preferably used at 3 to 10% by weight. The dextran sulfate sodium may be used at a molecular weight of 3,000 to 100,000 Da. More preferably, the dextran sulfate sodium used has a molecular weight of 5,000 to 30,000 Da.

My hybridization reagent may contain a denaturing agent. The hybridization reagent may contain, for example, formamide or dimethyl sulfoxide. The formamide or dimethyl sulfoxide has an action that weakens hydrogen bonds between nucleic acid bases. A-T and G-C have different numbers of hydrogen bonds, and, by controlling their binding affinities, an effect that improves the binding specificity in the hybridization can be expected. The concentration of formamide is preferably 1 to 50% by volume, more preferably 1 to 30% by volume. It is most preferably used at 3 to 25% by volume. The concentration of dimethyl sulfoxide is preferably 1 to 40% by volume, more preferably 1 to 20% by volume. It is most preferably used at 3 to 10% by volume.

My hybridization reagent may contain an inhibitor of non-specific adsorption to protein. Preferred examples of the inhibitor include bovine serum albumin (BSA). BSA can be expected to have an effect that improves the signal-to-noise ratio by inhibiting non-specific adsorption, which generates a background noise. The concentration of the non-specific-adsorption inhibitor such as BSA is preferably 1 to 100 mg/mL, more preferably 5 to 50 mg/mL. The inhibitor is most preferably used at 10 mg/mL.

My hybridization reagent may contain a substance useful to increase sensitivity of the hybridization reaction. For example, since air bubbles generated during the hybridization reaction may physically inhibit the hybridization reaction, the reagent may contain an antifoaming agent or the like that suppresses generation of air bubbles. Examples of the antifoaming agent include surfactants such as TWEEN 20 (trade name), TWEEN 60 (trade name), and TRITON X-100 (trade name); and silicone oils. The concentration of the antifoaming agent for its use is not limited, and is usually about 0.001 to 10% by weight, preferably about 0.01 to 1% by weight.

The composition of my hybridization reagent may be the same as a well-known composition except that the reagent contains my nucleic acid. One specific preparation example of the reagent may be "6×SSPE, 0.1% SDS, 25% formamide, 10 mg/mL BSA, 10% dextran sulfate sodium, and 15

μM poly-dG5", for which one may refer to a composition described in "Ku WC. et al., Biochemical and Biophysical Research Communications, 2004, vol. 315, issue 1, pp. 30-37".

I further provide a hybridization method for nucleic acid, the method comprising carrying out hybridization in the coexistence of the non-specific-binding inhibitor for my nucleic acid, or by using my hybridization reagent.

The hybridization method per se for nucleic acid may be carried out in the same manner as a well-known method except that my nucleic acid is made to coexist. For example, a method described in "Sambrook, J. et al. (1998) Molecular Cloning: A Laboratory Manual (2nd ed.), Cold Spring Harbor Laboratory Press, New York" may be used. More specifically, a target nucleic acid, and my non-specific-binding inhibitor or my hybridization reagent, may be added to a support on which a complementary-strand nucleic acid probe is preliminarily immobilized. Hybridization can then be carried out by incubation at a certain temperature. Before addition of my non-specific-binding inhibitor or my hybridization reagent, the target nucleic acid may be heat-denatured for a certain period of time at high temperature. By this, specificity of the nucleic acid binding can be further improved. Alternatively, a target nucleic acid, a complementary-strand nucleic acid probe, and my non-specific-binding inhibitor or my hybridization reagent, may be mixed together, and may then be incubated at a certain temperature to carry out hybridization, followed by immobilizing the complementary-strand nucleic acid probe on the support.

I still further provide a detection method for a nucleic acid, the method comprising the steps of: hybridizing a target nucleic acid with a nucleic acid capable of specific binding to the target nucleic acid, in the coexistence of the non-specific-binding inhibitor for my nucleic acid, or by using my hybridization reagent; and detecting a nucleic acid complex formed by the hybridization.

The step of hybridizing a target nucleic acid with a nucleic acid capable of specific binding thereto may be carried out by applying, as it is, the hybridization method for nucleic acid described above.

The step itself of detecting a nucleic acid complex formed by the hybridization step may be carried out by application of a well-known detection method for nucleic acid. For example, in the hybridization step, the target nucleic acid may be preliminarily labeled with a labeling molecule, to enable detection of the amount of the nucleic acid complex as the amount of the labeling molecule. Examples of labeling molecules that may be used therefor include fluorescent substances such as organic fluorescent dyes, phosphorescent dyes, quantum dots, and fluorescent proteins; chemiluminescent proteins; radioisotopes; redox species capable of giving and receiving electrons; enzymes themselves such as alkaline phosphatase and horseradish peroxidase; and nucleic acid monomers containing these labeling molecules. In a nucleic acid monomer containing a labeling molecule, labeling of the target nucleic acid is possible by enzymatically introducing the monomer to an end of the target nucleic acid.

For the detection of the nucleic acid complex, a fluorescent substance is preferably used as a labeling molecule from the viewpoint of sensitivity and simplicity. In this example, the amount of the nucleic acid complex can be measured as a signal value of a fluorescence emitted from the fluorescent substance, using a fluorescence microscope, plate reader or the like.

In the detection of the nucleic acid complex, binding between the target nucleic acid and a nucleic acid probe capable of specifically binding thereto can also be detected as a change in the fluorescence wavelength of a nucleic acid intercalator. Examples of the nucleic acid intercalator include ethidium bromide, "SYBR (registered trademark) Green", and substitutes thereof. For example, after a hybridization step using a nucleic acid array, the nucleic acid array on which a complex between the target nucleic acid and the nucleic acid probe is formed may be immersed in a nucleic acid intercalator solution, and then the array may be washed with a buffer or the like. Thereafter, the amount of the nucleic acid complex can be measured as a signal value of a fluorescence emitted from the nucleic acid intercalator, using a fluorescence microscope or a plate reader.

The detection of the complex nucleic acid may be carried out by a known method such as in situ hybridization, colony hybridization, dot blotting, Southern blotting, or Northern blotting, or by using a nucleic acid array (DNA microarray, DNA chip or the like) wherein a nucleic acid (nucleic acid probe) which specifically binds the target nucleic acid, and which has a base sequence complementary to the target nucleic acid, is immobilized on a support.

As the nucleic acid array, a commercially available product may be used. Examples of such a product include "GENECHIP (registered trademark) Arrays", manufactured by Affymetrix Inc.; oligo DNA chips manufactured by Agilent Technologies, Inc.; and "3D-GENE (registered trademark)", manufactured by Toray Industries, Inc. It is preferred to use "3D-GENE (registered trademark)", manufactured by Toray Industries, since it uses a resin support, with which physical adsorption of nucleic acid can be reduced, and since it achieves improved stirring efficiency for the hybridization solution by employing microbeads for the stirring.

EXAMPLES

My inhibitors, reagents and methods are described concretely by way of the following Examples. However, this disclosure is not limited to the scope of the Examples, and the Examples merely describe some of the large number of variations that can be devised.

Examples 1 and 2, Comparative Examples 1 and 2

As a nucleic acid array, a DNA microarray manufactured by Toray Industries, Inc. "3D-GENE (registered trademark) human miRNA oligo chip (compatible with miRBase release 21)" was used. As a target nucleic acid, hsa-miR-6858-5p (miRBase Accession No. MIMAT0027616, SEQ ID NO:3), which is a miRNA that potentially causes cross-hybridization, was selected. These were used to evaluate the cross-hybridization-inhibiting effect of the non-specific-binding inhibitor for my nucleic acid in a hybridization reaction.

The target nucleic acid hsa-miR-6858-5p was chemically synthesized as a 5'-end phosphate group-modified product (custom synthesis by Fasmac Co., Ltd.; HPLC purification grade). The target nucleic acid was dissolved in distilled water at 2.5 fmol/μL, and a 5-fmol portion thereof was subjected to fluorescence labeling using a "3D-GENE (registered trademark) miRNA labeling kit" (Toray Industries, Inc.). Thereafter, according to the standard protocol of the kit, hybridization was carried out using the nucleic acid array.

As a non-specific-binding inhibitor for nucleic acid, "poly-dG5" (custom synthesis by Fasmac Co., Ltd.; reverse-phase column purification grade) was used. The inhibitor was dissolved in "miRNA Hybridization buffer V3" to a final concentration of 1 μM (Example 1) or 10 μM (Example 2), to prepare hybridization solutions to be used in the hybridization.

In addition, salmon sperm DNA (Invitrogen; catalog number, 15632011) was dissolved to a final concentration of 92 μg/mL (Comparative Example 1), or "Random Primer (N) 9" (Takara Bio Inc; catalog number, 3802) was dissolved to a final concentration of 6.5 μg/mL (corresponding to 2.2 μM) (Comparative Example 2), to prepare hybridization solutions as controls for comparison to be used in the hybridization.

The DNA microarray after the hybridization was subjected to a "Microarray Scanner" (Toray Industries, Inc.), to measure the fluorescence intensity. The scanner was used with the following settings: laser output, 100%; photomultiplier voltage, AUTO. Using digitization software "3D-Gene Extraction" (Toray Industries, Inc.), the fluorescence intensity of each spot in the obtained scanned image was digitized as a signal value. The ratio between the signal value of the target nucleic acid and the signal value of hsa-miR-4498 (miRBase Accession No. MIMAT0019033, SEQ ID NO:4), which exhibited the highest signal among the signals detected as a result of cross-hybridization (signal value of hsa-miR-6858-5p/signal value of hsa-miR-4498), was calculated as the S/N ratio.

The results are shown in FIG. 1. Compared to the S/N ratio (1.58) when the non-specific-binding inhibitor for nucleic acid was not added, the S/N ratio when the salmon sperm DNA was added was improved to 2.78, indicating production of a cross-hybridization-inhibiting effect. The S/N ratio when Random Primer (N) 9 was added was 1.33, indicating no production of a cross-hybridization-inhibiting effect. In contrast, when my non-specific-binding inhibitor, poly-dG5, was used at the concentration of 1 μM or 10 μM, an S/N ratio of 1.95 or 2.47, respectively, was obtained, indicating that the cross-hybridization-inhibiting effect increased as the concentration of the inhibitor added increased. Thus, poly-dG5 was found to exhibit a cross-hybridization-inhibiting effect at least at a concentration of not less than 1 μM.

Examples 3 to 8

Hybridization of the target nucleic acid hsa-miR-6858-5p was carried out in the same manner as in Example 1 except that, in the preparation of the hybridization solution to be used for the hybridization, "poly-dG5" (custom synthesis by Fasmac Co., Ltd.; HPLC purification grade) was added to a final concentration of 10 μM (Example 3) or 15 μM (Example 4);

"poly-dG7" (custom synthesis by Fasmac Co., Ltd.; HPLC purification grade) was added to a final concentration of 10 μM (Example 5) or 15 μM (Example 6); or "poly-dG10" (custom synthesis by Fasmac Co., Ltd.; HPLC purification grade; SEQ ID NO:1) was added to a final concentration of 10 μM (Example 7) or 15 μM (Example 8);

as a non-specific-binding inhibitor for nucleic acid, to evaluate the cross-hybridization-inhibiting effect.

Figure 2:
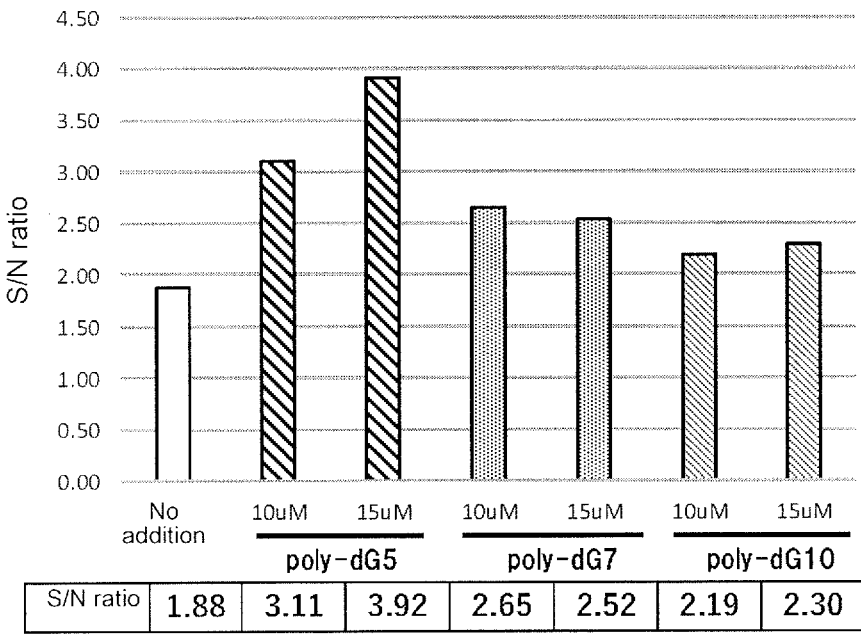
FIG. 2 shows the cross-hybridization-inhibiting effects of poly-dG5, poly-dG7, and poly-dG10 (Examples 3 to 8; poly-dG10 is SEQ ID NO:1).

The results are shown in FIG. 2. When poly-dG5 was added at 10 μM or 15 μM, the S/N ratio was improved to 3.11 or 3.92, respectively, indicating production of a cross-hybridization-inhibiting effect higher than that of the salmon sperm DNA (Comparative Example 1). When poly-dG7 was added at 10 μM or 15 μM, and when poly-dG10 was added at 10 μM or 15 μM, the S/N ratio was improved compared to when no inhibitor was added. From these results, I found that nucleic acids having a sequence of consecutive guanine bases with a base length of 5 to 10 have a cross-hybridization-inhibiting effect, and that poly-dG5 (15 μM) exhibits a remarkably high cross-hybridization-inhibiting effect.

Examples 9 to 12

Hybridization of the target nucleic acid hsa-miR-6858-5p was carried out in the same manner as in Example 1 except that, in the preparation of the hybridization solution to be used for the hybridization, "poly-dG5" (custom synthesis by Fasmac Co., Ltd.; reverse-phase column purification grade) (Example 9), "GGAGG" (custom synthesis by Fasmac Co., Ltd.; HPLC purification grade) (Example 10), "GGGAG" (custom synthesis by Fasmac Co., Ltd.; HPLC purification grade) (Example 11), or "TGGGG" (custom synthesis by Fasmac Co., Ltd.; HPLC purification grade) (Example 12) was added to a final concentration of 15 μM as a non-specific-binding inhibitor for nucleic acid, to evaluate the cross-hybridization-inhibiting effect.

Figure 3:
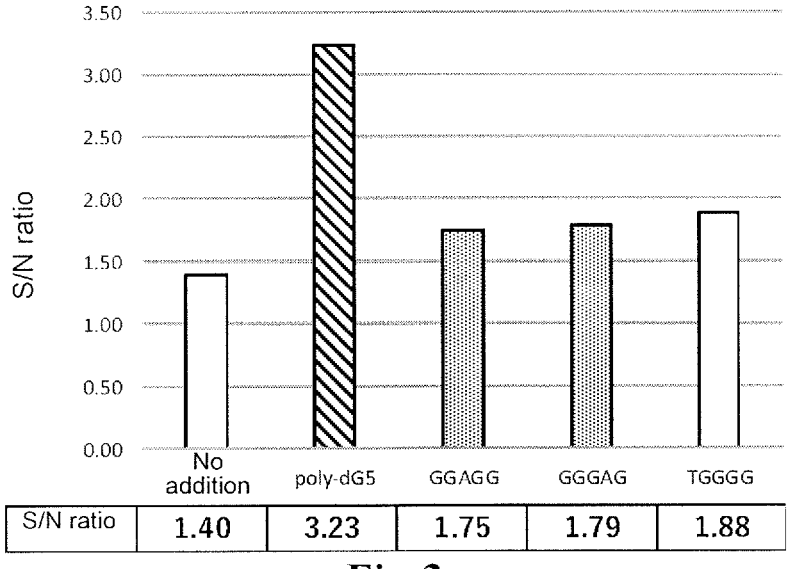
FIG. 3 shows the cross-hybridization-inhibiting effects of poly-dG5, GGAGG, GGGAG, and TGGGG (Examples 9 to 12).

The results are shown in FIG. 3. Any of the non-specific-binding inhibitors for my nucleic acid improved the S/N ratio compared to when no inhibitor was added. From these results, I found that nucleic acids containing guanine bases at high ratios generally have a cross-hybridization-inhibiting effect similarly to the nucleic acids composed of guanine bases alone such as poly-dG5, which showed a high cross-hybridization-inhibiting effect.

Example 13

Influence of a difference in the production lot of the non-specific-binding inhibitor for my nucleic acid on the cross-hybridization-inhibiting effect was evaluated.

As a non-specific-binding inhibitor for nucleic acid, "poly-dG5" (custom synthesis by Fasmac Co., Ltd.; reverse-phase column purification grade) was provided from four different production lots. Hybridization solutions were prepared in the same manner as in Example 4 (or Example 9) such that each solution contains each lot at a final concentration of 15 μM. Each lot was subjected to hybridization four times (N=4; N=16 in total in the measurement for the four lots).

Figure 4:
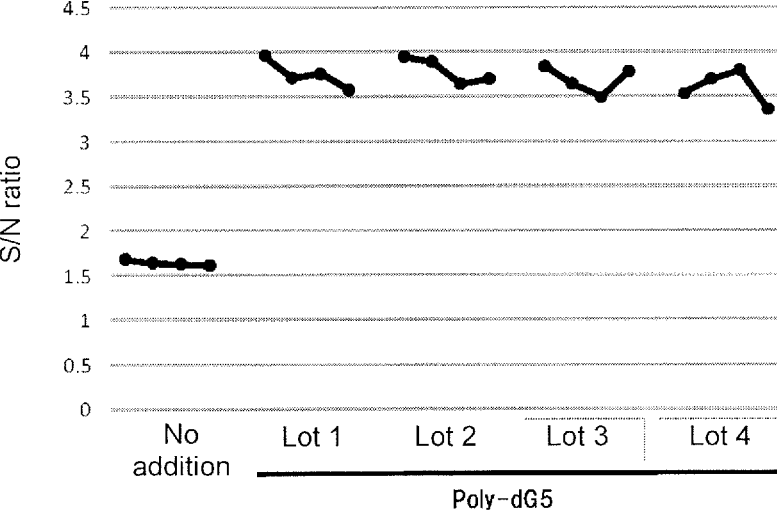
FIG. 4 shows the stability of the cross-hybridization-inhibiting effect of poly-dG5 among lots (Example 13).

The results are shown in FIG. 4. The average and the CV value of the S/N ratio of each lot (N=4) of poly-dG5 were as follows. In lot 1, the average was 3.75, and the CV value was 4.25%. In lot 2, the average was 3.79, and the CV value was 3.82%. In lot 3, the average was 3.69, and the CV value was 4.22%. In lot 4, the average was 3.60, and the CV value was 5.33%. As a whole, the four lots showed an average of 3.71 and a CV value of 4.47%. The non-specific-binding inhibitor for my nucleic acid exhibited no large difference in the performance among the production lots, indicating production of a stable cross-hybridization-inhibiting effect.

Comparative Example 3

As a non-specific-binding inhibitor for nucleic acid that has been conventionally used, salmon sperm DNA (Invitrogen; catalog number, 15632011) was provided from four different production lots. Hybridization solutions were prepared in the same manner as in Example 13 such that each solution contains each lot at a final concentration of 92 μg/mL. Each lot was subjected to hybridization four times (N=4; N=16 in total in the measurement for the four lots).

Figure 5:
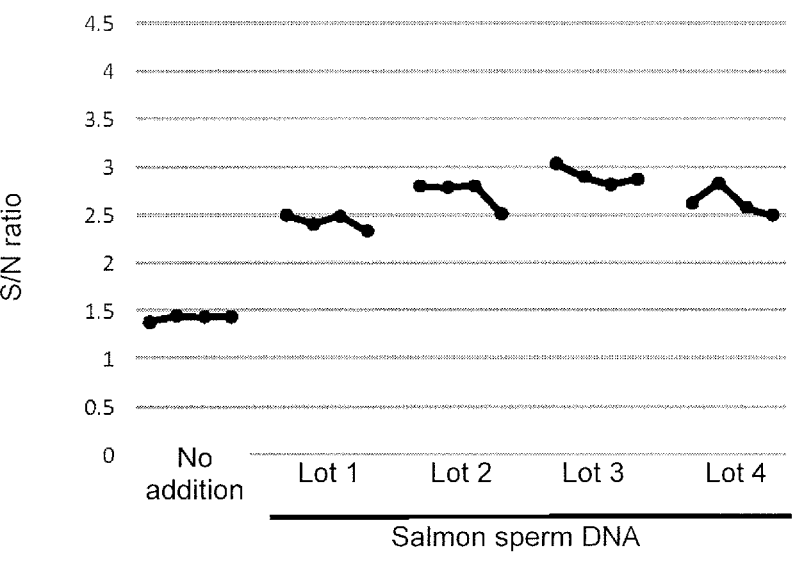
FIG. 5 shows the instability of the cross-hybridization-inhibiting effect of salmon sperm DNA among lots (Comparative Example 3).

The results are shown in FIG. 5. The average and the CV value of the S/N ratio of each lot (N=4) of salmon sperm DNA were as follows. In lot 1, the average was 2.43, and the CV value was 3.24%. In lot 2, the average was 2.72, and the CV value was 5.26%. In lot 3, the average was 2.90, and the CV value was 3.20%. In lot 4, the average was 2.63, and the CV value was 5.51%. As a whole, the four lots showed an average of 2.67 and a CV value of 7.75%. It was shown that salmon sperm DNA, which has been conventionally used, exhibits large lot-to-lot differences in the cross-hybridization-inhibiting effect compared to the non-specific-binding inhibitor for my nucleic acid.

---

SEQUENCE LISTING FREE TEXT

| | |
|---|---|
| SEQ ID NO: 1: | Designed Sequence, poly-dG10 |
| SEQ ID NO: 2: | Designed Sequence |

---

14

The invention claimed is:

1. A method of hybridizing a target nucleic acid comprising:

hybridizing the target nucleic acid with a nucleic acid for specific binding to the target nucleic acid in a hybridization solution, the hybridization solution comprising a non-specific-binding inhibitor for the nucleic acid, and wherein the non-specific-binding inhibitor is not immobilized on a substrate;

the non-specific-binding inhibitor for the nucleic acid consisting essentially of a nucleic acid having a base length of five bases, six bases, seven bases, eight bases, nine bases, 10 bases, or 11 bases, and having from 5 to 10 consecutive guanine bases, wherein non-specific binding is decreased compared to when the non-specific-binding inhibitor is not added wherein the non-specific binding inhibitor is DNA, and wherein the target nucleic acid is human miRNA.

2. A method of detecting a target nucleic acid comprising:

a hybridization step of hybridizing the target nucleic acid with a nucleic acid for specific binding to the target nucleic acid in a hybridization solution, wherein a non-specific-binding inhibitor for a nucleic acid is contained in the hybridization solution and not immobilized on a substrate;

---

SEQUENCE LISTING

```
<160> NUMBER OF SEQ ID NOS: 4

<210> SEQ ID NO 1
<211> LENGTH: 10
<212> TYPE: DNA
<213> ORGANISM: Artificial Sequence
<220> FEATURE:
<223> OTHER INFORMATION: Designed Sequence, poly-dG10

<400> SEQUENCE: 1
gggggggggg                                                        10

<210> SEQ ID NO 2
<211> LENGTH: 11
<212> TYPE: DNA
<213> ORGANISM: Artificial Sequence
<220> FEATURE:
<223> OTHER INFORMATION: Designed Sequence

<400> SEQUENCE: 2
gggggggggg g                                                      11

<210> SEQ ID NO 3
<211> LENGTH: 22
<212> TYPE: RNA
<213> ORGANISM: Homo sapiens

<400> SEQUENCE: 3
gugaggaggg gcuggcaggg ac                                          22

<210> SEQ ID NO 4
<211> LENGTH: 22
<212> TYPE: RNA
<213> ORGANISM: Homo sapiens

<400> SEQUENCE: 4
ugggcuggca gggcaagugc ug                                          22
``` the non-specific-binding inhibitor consisting essentially of a nucleic acid having a base length of five bases, six bases, seven bases, eight bases, nine bases, 10 bases, or 11 bases, and having from 5 to 10 consecutive guanine bases wherein non-specific binding is decreased compared to when the non-specific binding inhibitor is not added;

wherein the non-specific binding inhibitor is DNA, wherein the target nucleic acid is human miRNA, and further comprising a detection step of detecting a nucleic acid complex formed by the hybridization step.

3. The method according to claim 2, wherein a nucleic acid capable of specifically binding to the target nucleic acid is immobilized on an array.

4. The method of claim 1, wherein the nucleic acid of the non-specific-binding inhibitor has a base length of 5 to 7 bases.

5. The method of claim 1, wherein the 5 to 10 consecutive guanine bases comprise a methylated guanine bases.

6. The method of claim 1, wherein the non-specific-binding inhibitor comprises a nucleic acid having five consecutive guanine bases.

7. The method of claim 1, wherein the non-specific-binding inhibitor comprises a nucleic acid consisting of guanine bases.

8. The method of claim 1, wherein hybridization is carried out in the presence of the non-specific-binding inhibitor for the nucleic acid at a concentration of 0.3 pM to 100 pM.

9. The method of claim 2, wherein hybridization is carried out in the presence of the non-specific-binding inhibitor at a concentration of 0.3 μM to 100 μM.

* * * * *